United States Patent [19]

Kolar et al.

[11] Patent Number: 5,071,836
[45] Date of Patent: Dec. 10, 1991

[54] COMPETITIVE GONADOLIBERIN ANTAGONISTS

[75] Inventors: Cenek Kolar, Marburg; Wolfgang König, Hofheim am Taunus; Jurgen K. Sandow, Königstein/Taunus, all of Fed. Rep. of Germany

[73] Assignee: Hoechst Aktiengesellschaft, Frankfurt am Main, Fed. Rep. of Germany

[21] Appl. No.: 448,904

[22] Filed: Dec. 12, 1989

[30] Foreign Application Priority Data

Dec. 14, 1988 [DE] Fed. Rep. of Germany ....... 3842010

[51] Int. Cl.$^5$ .................... C07K 7/06; A61K 37/02
[52] U.S. Cl. .................................. 514/15; 514/8; 530/328
[58] Field of Search ................. 514/15.8; 530/328

[56] References Cited

U.S. PATENT DOCUMENTS

| | | | |
|---|---|---|---|
| 4,118,483 | 10/1978 | König et al. | 424/177 |
| 4,504,467 | 3/1985 | Molloy et al. | 424/118 |
| 4,530,920 | 7/1985 | Nestor et al. | 514/15 |
| 4,569,927 | 2/1986 | Rivier et al. | 514/15 |

FOREIGN PATENT DOCUMENTS

| | | |
|---|---|---|
| 0097031 | 12/1983 | European Pat. Off. |
| 877561 | 10/1987 | South Africa . |
| 1458685 | 12/1976 | United Kingdom . |
| WO89/09786 | 10/1989 | World Int. Prop. O. |

OTHER PUBLICATIONS

Folkers et al., Z. Naturforsch, 42b, (1987), 101–106.
Ljungqvist et al., Biochem. Biophys. Res. Commun., 148, (1987), 849–856.
Bajusz et al., Proc. Natl. Acad. Sci., U.S.A., 85, (1988), 1637–1641.
Hocart et al., J. Med. Chem., 30, (1987), 735–739.
Nestor, Jr. et al., LHRH and its Derivatives, pp. 24–35 (1984).
Dutta, Drugs of the Future, vol. 13, No. 8, pp. 761–787 (1988).
Phillips et al., Life Sciences, vol. 41, No. 17, pp. 2017–2022 (1987).
Nestor, Jr. et al., J. Med. Chem., vol. 31, No. 1, pp. 65–72, (1988).

*Primary Examiner*—Lester L. Lee
*Assistant Examiner*—Avis M. Davenport
*Attorney, Agent, or Firm*—Finnegan, Henderson, Farabow, Garrett, and Dunner

[57] ABSTRACT

Peptides of the formula

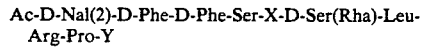

Ac-D-Nal(2)-D-Phe-D-Phe-Ser-X-D-Ser(Rha)-Leu-Arg-Pro-Y in which X represents Tyr or His and Y represents Gly-NH$_2$, D-Ala-NH$_2$, Azgly-NH$_2$ or NH—C$_2$H$_5$ are competitive antagonists of Gn-RH. They are used for the treatment of gonadotropin- and steroid-dependent diseases and are prepared by known methods of peptide chemistry.

4 Claims, No Drawings

COMPETITIVE GONADOLIBERIN ANTAGONISTS

DESCRIPTION

Naturally occurring gonadoliberins (Gn-RH) of various species are decapeptides of the following structures:

| | |
|---|---|
| h-, p-, o- | Pgl—His—Trp—Ser—Tyr—Gly—Leu—Arg—Pro—Gly—NH$_2$ |
| g-Gn—RH-I | Pgl—His—Trp—Ser—Tyr—Gly—Leu—Gln—Pro—Gly—NH$_2$ |
| g-Gn—RH-II | Pgl—His—Tyr—Ser—His—Gly—Trp—Tyr—Pro—Gly—NH$_2$ |
| sa-Gn—RH | Pgl—His—Trp—Ser—Tyr—Gly—Trp—Leu—Pro—Gly—NH$_2$ |
| pe-Gn—RH | Pgl—His—Tyr—Ser—Leu—Glu—Trp—Lys—Pro—Gly—NH$_2$ |

[h (human), p (pig), o (sheep): Biochem. Biophys. Res. Commun. 43 (1971) 1334; g (chicken I): South Africa J. Science 78 (1982) 124; g (chicken II): Proc. Natl. Acad. Sci. USA 81 (1984) 3874; sa (salmon): Proc. Natl. Acad. Sci. USA 80 (1983) 2794; pe (lamprey): J. Biol. Chem. 261 (1986) 4812–4819].

In mammals, Gn-RH is mainly formed in the hypothalamus and brings about release of lutropin (LH) and follitropin (FSH) in the pituitary.

Competitive antagonists of Gn-RH inhibit, via blockade of Gn-RH receptors, the formation of LH and FSH and thus also the synthesis of estrogen in female animals and women or testosterone in male animals and men. Many Gn-RH antagonists have already been described in the literature [J. J. Nestor, Jr. et al. in: Publishers B.V. 1984, pp. 24–35; A. S. Dutta, Drugs of the Future 13 (1988) 761–787], most of which contain a basic amino acid in position 6. This basic charge in position 6 makes the peptides more soluble in water. A negative side effect of this basic group is, however, a histamine-releasing action. The "Nal-Glu", in which the Arg in position 5 has been displaced and D-4-p-methoxybenzoyl-2-amino-butyric acid is present in position 6, has a greatly reduced histamine release [A. Phillips et al., Life Sci. 41 (1987) 2017–2022]. Less basic substitutions in position 6, such as, for example, D-nicotinoyl-lysine [K. Folkers et al., Z. Naturforsch. 42b (1987) 101–106; A. Ljungqvist et al., Biochem. Biophys. Res. Commun. 148 (1987) 849–856], D-citrulline or D-homocitrulline [S. Bajusz et al. Proc. Natl. Acad. Sci. USA 85 (1988) 1637–1641] likewise diminish the histamine release.

In EP-A 263,521 (HOE 86/F 253), both Gn-RH agonists and Gn-RH antagonists with favorable properties were obtained by substitution with glycosylated sugars. It was possible in this way on the one hand to increase the solubility in water, and on the other hand to reduce the anaphylactic action, which was observed particularly with Gn-RH antagonists.

In a further examination of these glycosylated Gn-RH derivatives, we have found, surprisingly, that specific compounds of the general formula I antagonize endogenous Gn-RH particularly strongly and thus reduce the serum level of luteotropic hormone (LH) and the follicle-stimulating hormone (FSH) of testosterone and of estrogen.

The invention relates to peptides of the general formula I

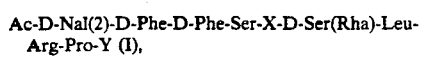

Ac-D-Nal(2)-D-Phe-D-Phe-Ser-X-D-Ser(Rha)-Leu-Arg-Pro-Y (I), in which
Ac represents acetyl,
D-Nal(2) represents 3-(2-naphthyl)-D-alanine,
D-Phe represents D-phenylalanine,
Ser represents L-serine,
X represents L-tyrosine (Tyr) or L-histidine (His),
D-Ser(Rha) represents O-(α-L-rhamnopyranos-yl)-D-serine,
Leu represents L-leucine,
Arg represents L-arginine,
Pro represents L-proline and
Y represents glycinamide (Gly-NH$_2$), D-alaninamide (D-Ala-NH$_2$), azaglycinamide (Azgly-NH$_2$) or NH-C$_2$H$_5$,
as well as the physiologically tolerated salts thereof.

Particularly preferred antagonists are compounds in which Tyr or His represents X and Azgly-NH$_2$ or D-Ala-NH$_2$ represents Y.

D-Phe in position 2 and 3 in place of D-pCl-Phe$^2$ and D-Trp$^3$ in Detirelix [J. J. Nestor, Jr., J. Med. Chem. 31 (1988) 65–72] or D-pCl-Phe$^2$ and D-3-pyridyl-alanine in position 3 in "Nal-Glu" has the advantage of being less costly. Because the chemistry of D-Phe is less problematic, the synthesis is also more straightforward (fewer byproducts) and the products are more stable.

The combination D-Phe$^2$, D-Phe$^3$ has already been employed in the antagonist Ac-D-Nal(2)-D-Phe-D-Phe-Ser-Tyr-D-Arg-Phe-Arg-Pro-D-Ala-NH$_2$, where it showed a somewhat lower antiovulatory action than the compound with D-pCl-Phe$^2$ and D-Trp$^3$ [S. J. Hocart et al., J. Med. Chem. 30 (1987) 735–739].

The peptides can be prepared, using the general methods of peptide chemistry (Houben-Weyl, Methoden der Organischen Chemie (Methods of Organic Chemistry), volume 15), stepwise from the C-terminal end or by segment condensation, for example by fragment condensation, which comprises condensing a fragment with an N-terminal free amino group with a fragment with a C-terminal free carboxyl group, eliminating one or more protective groups temporarily introduced where appropriate to protect functional groups, and converting the peptide obtained in this way into its physiologically tolerated salt where appropriate. One possible synthesis of the serine glycosides is described in EP-A 263,521.

In order to minimize the racemization which is possible in the segment condensation, it is preferable to use for this dicyclohexylcarbodiimide (DCC) with the addition of 3-hydroxy-4-oxo-3,4-dihydro-1,2,3-benzotriazine (HOObt). The amino-protective groups which are preferably employed are the Z radical which can be eliminated by catalytic hydrogenation or the Fmoc radical which can be eliminated by secondary amines. The imidazole ring of the histidine is preferably protected by the 2,4-dinitrophenyl(Dnp) radical, which can be eliminated by mercaptans or hydrazine.

A segment coupling in accordance with the scheme (1-4)+(5-10)→(1-10)

has proven particularly favorable. The synthesis is illustrated by the following 2 reaction scheme.

the absorption from the gastrointestinal tract is only low and daily parenteral administration is inappropriate for patients.

A metered atomizer is used to spray, via a spray nozzle, into the nose about 0.02–0.2 ml of a buffer solution

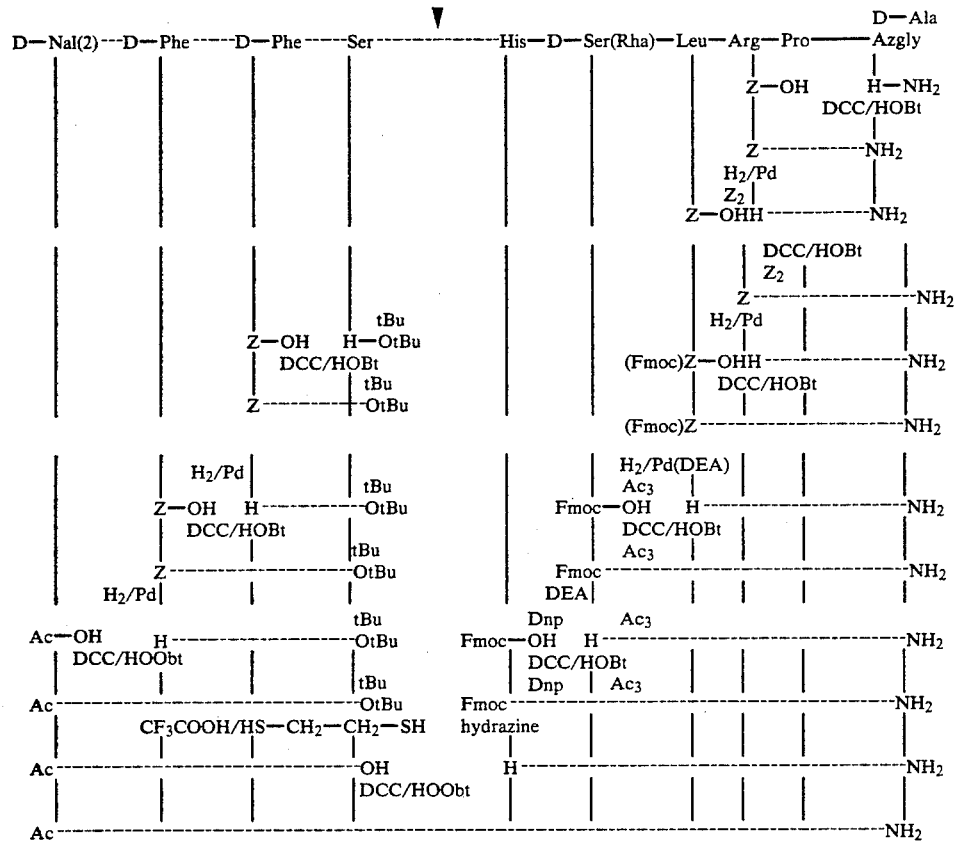

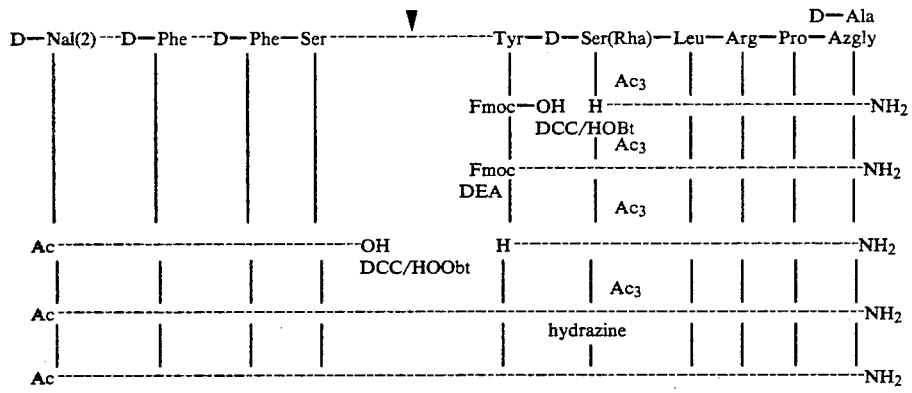

The Gn-RH antagonists according to the invention can be employed like high-dose Gn-RH agonists in gonadotropin-and steroid-dependent diseases. However, the advantage of the antagonists over the agonists is that the initial stimulation phase of the agonists is avoided.

The preferred forms for administration to humans is intranasal administration or the use of implants, because in which the necessary amount of the active substance is dissolved. The dosages on parenteral administration can be reduced by about one power of ten from the intranasal dose.

The antagonists according to the invention are administered intranasally in doses of 1–10 mg to adult humans. The single dose in implants is about 5–50 mg for a period of 4–8 weeks in each case. As little as 0.1–1 mg per administration suffices on parenteral administration.

The peptides according to the invention have been tested for an atrophic action on androgen-dependent organs and for an LH- and testosterone-lowering action in the serum and blood of male rats by continuous infusion (MINIPUMPS).

The most active were the compounds of Examples 1 and 2. The compound of Example 3 is still highly active, whereas the compound of Example 4 showed the weakest action in this group.

Other abbreviations used:

| | |
|---|---|
| HOBt | 1-hydroxybenzotriazole |
| DEA | diethylamine |

EXAMPLE 1

Ac-D-Nal(2)-D-Phe-D-Phe-Ser-His-D-Ser(Rha)-Leu-Arg-Pro-Azgly-NH$_2$

1a) Z-D-Phe-Ser(tBu)-OtBu 9.07 ml of N-ethylmorpholine and 16.05 g of DCC are added at 0° C. to a solution of 21.2 g of Z-D-Phe-OH, 9.6 g of HOBt and 17.9 g of HCl.H-Ser(tBu)-OtBu in 150 ml of dimethylformamide. The mixture is left to stir at 0° C. for one hour and to stand at room temperature overnight. The precipitate is filtered off with suction, and the filtrate is concentrated. The residue is partitioned between ethyl acetate and water. The ethyl acetate phase is extracted by shaking successively with saturated NaHCO$_3$ solution, KHSO$_4$/K$_2$SO$_4$ solution and water, dried over Na$_2$SO$_4$ and concentrated. The substance crystallizes after trituration with petroleum ether.

Yield: 23.4 g.
Melting point 79°–81° C.
$[\alpha]^{21}_D = +20.6°$ (c=1, in methanol).

1b) H-D-Phe-Ser(tBu)-OtBu.HCl 22.0 g of Z-Phe-Ser(tBu)-OtBu are dissolved in methanol and catalytically (Pd/carbon) hydrogenated at pH 4.5 with the addition of methanolic hydrochloric acid by means of an autotitrator. After the hydrogenation is complete, the catalyst is filtered off with suction through kieselguhr, and the filtrate is concentrated. The residue is triturated with diethyl ether. The substance solidifies and can be filtered off with suction.

Yield: 15.6 g.
Melting point 154°–156° C.
$[\alpha]^{22}_D = -24.7°$ (C=1, in methanol).

1c) Z-D-Phe-D-Phe-Ser(tBu)-OtBu 4.71 ml of N-ethylmorpholine and 7.98 g of DCC are added at 0° C. to a solution of 10.69 g of Z-D-Phe-OH, 14.5 g of H-D-Phe-Ser(tBu)-OtBu.HCl and 4.89 g of HOBt in 150 ml of dimethylformamide. The mixture is left to stir at 0° C. for 1 hour and to stand at room temperature overnight. The precipitate is filtered off with suction, and the filtrate is concentrated. The residue is partitioned between ethyl acetate and water. The ethyl acetate phase is extracted by shaking successively with saturated NaHCO$_3$ solution, KHSO$_4$/K$_2$SO$_4$ solution and water, dried over Na$_2$SO$_4$ and concentrated. The oil crystallizes from isopropanol/petroleum ether.

Yield: 19.2 g.
Melting point 91°–92° C.
$[\alpha]^{22}_D = +27.5°$ (c=1, in methanol).

1d) H-D-Phe-D-Phe-Ser(tBu)-OtBu.HCl 18.0 g of Z-D-Phe-D-Phe-Ser(tBu)-OtBu are dissolved in methanol and catalytically hydrogenated as in Example 1b). The residue is triturated with diethyl ether and filtered off with suction.

Yield 13.15 g.
Melting point 143°–144° C.
$[\alpha]^{23}_D = -2.7°$ (c=1, in methanol).

1e) Ac-D-Nal(2)-D-Phe-D-Phe-Ser(tBu)-OtBu 2.56 ml of N-ethylmorpholine and 4.4 g of DCC are added at 0° C. to a solution of 11 g of HCl.H-D-Phe-D-Phe-Ser-(tBu)-OtBu, 5.16 g of Ac-D-Nal(2)-OH and 3.28 g of HOObt in 150 ml of dimethylformamide, and the mixture is left to stir at 0° C. for 1 hour and to stand at room temperature overnight. The precipitate is filtered off with suction, and the filtrate is concentrated. The residue is worked up as in Example 1a).

Yield: 10.56 g.
Melting point 187° C.
$[\alpha]^{20}_D = +11.0°$ (c=1, in methanol).

1f) Ac-D-Nal(2)-D-Phe-D-Phe-Ser-OH 10 g of Ac-D-Nal(2)-D-Phe-D-Phe-Ser(tBu)-OtBu are dissolved in a mixture of 40 ml of 90% strength aqueous trifluoroacetic acid and 1.6 ml of 1,2-dimercaptoethane. The mixture is left to stand at room temperature for one hour and is concentrated. The residue is triturated with water and dried under high vacuum.

Yield: 9.84 g.
$[\alpha]^{23}_D = +14.2°$ (c=1, in methanol).

1g)
Ac-D-Nal(2)-D-Phe-D-Phe-Ser-His-D-Ser(Rha)-Leu-Arg-Pro-Azgly-NH$_2$ 110 mg of DCC are added at 0° C. to a solution of 320 mg of Ac-D-Nal(2)-D-Phe-D-Phe-Ser-OH, 424.2 mg of H-His-D-Ser(Rha)-Leu-Arg(HCl)-Pro-Azgly-NH$_2$ and 81.5 mg of HOObt in 7 ml of dimethylformamide. The mixture is stirred at 0° C. for 1 hour and left to stand at room temperature overnight. The precipitate is filtered off with suction, and the filtrate is concentrated. The residue is taken up in 100 ml of pentanol and extracted three times wit saturated NaHCO$_3$ solution. The pentanol phase is neutralized with 1N HCl and concentrated. The residue is triturated with ethyl acetate and filtered off with suction.

Yield: 580 mg.
The substance is dissolved in 120 ml of 10% strength acetic acid. The solution is filtered through 40 ml of a weakly basic ion exchanger (acetate form) and eluted with water. The eluate fractions which contain the peptide are combined and freeze-dried.

Yield: 468 mg.
The 468 mg of crude substance obtained above are purified by chromatography on an alkylated dextran gel. The eluent used was a mixture of 4,300 ml of water, 430 ml of n-butanol and 350 ml of glacial acetic acid.

Yield: 276 mg.
$[\alpha]^{22}_D = -53.2°$ (c=1, in water).
Content of peptide base: 77.7%

EXAMPLE 2

Ac-D-Nal-D-Phe-D-Phe-Ser-His-D-Ser(Rha)-Leu-Arg-Pro-D-Ala-NHz acetate 110 mg of DCC are added at 0° C. to a solution of 320 mg of Ac-D-Nal-D-Phe-D-Phe-Ser-OH, 499 mg of H-His-D-Ser(Rha)-Leu-Arg-Pro-D-Ala-NH$_2$ tosylate and 81.5 mg of HOObt in 7 ml of dimethylformamide. The mixture is left to stir at 0° C. for 1 hour and subsequently at room temperature. The next day the precipitate is filtered off with suction, and the filtrate is concentrated. The residue is partitioned between pentanol and saturated NaHCO$_3$ solution. The pentanol phase is washed with NaHCO$_3$ solution and water and concentrated under high vacuum. The residue is triturated with ethyl acetate, filtered off with suction and dried.

Yield: 650 mg.

The substance obtained above is dissolved in about 40 ml of 10% strength acetic acid, and the solution is filtered to remove insolubles and chromatographed on 40 ml of a weakly basic ion exchanger (in the acetate form). Water is used for elution. The fractions which contained the substance were combined and freeze-dried.

Yield: 460 mg.
Purification in analogy to Example 1g).
Yield: 285 mg
$[\alpha]^{23}_D = -52.6°$ (c=1, in water).
Content of peptide base: 92%.

EXAMPLE 3

Ac-D-Nal-D-Phe-D-Phe-Ser-Tyr-D-Ser(Rha)-Leu-Arg-Pro-Azgly-NH$_2$

3a) H-Tyr-D-Ser(Rha)-Leu-Arg-Pro-Azgly-NH$_2$·HCl 1 ml of hydrazine hydrate is added to a solution of 1 g of H-Tyr-D-Ser[Rha(Ac$_3$)]-Leu-Arg-Pro-Azgly-NH$_2$·HCl in 10 ml of dimethylacetamide, and the mixture is stirred at room temperature for 4 hours. The clear solution is subsequently concentrated, and the residue is triturated with diethyl ether and methyl tert.-butyl ether, filtered off with suction and dried.

Yield: 0.9 g. $[\alpha]^{22}_D = -38.8°$ (c=1, in methanol).

3b)
Ac-D-Nal-D-Phe-D-Phe-Ser-Tyr-D-Ser(Rha)-Leu-Arg-Pro-Azgly-NH$_2$ acetate 110 mg of DCC are added at 0° C to a solution of 320 mg of Ac-D-Nal-D-Phe-D-Phe-Ser-OH, 419 mg of H-Tyr-D-Ser(Rha)-Leu-Arg-Pro-Azagly-NH$_2$·HCl and 81.5 mg of HOObt in 7 ml of dimethylformamide. The mixture is stirred at 0° C. for 1 hour and at room temperature overnight. The precipitate is filtered off with suction, and the filtrate is concentrated. The residue is partitioned between 400 ml of pentanol and 100 ml of saturated NaHCO$_3$ solution. Insolubles (2nd precipitate: already contains desired substance) are filtered off with suction. The pentanol phase is washed with saturated NaHCO$_3$ solution and water and concentrated. The residue is combined with the 2nd precipitate (yield: 375 mg) and purified by chromatography on silica gel. The eluent used was a 70:40:3:3 mixture of methylene chloride:methanol:water:acetic acid.

Yield: 118 mg.
$[\alpha]^{21}_D = -96.9°$ (c=1, in water).
Content of peptide base: 70%.

EXAMPLE 4

Ac-D-Nal-D-Phe-D-Phe-Ser-Tyr-D-Ser(Rha)-Leu-Arg-Pro-NH-C$_2$H$_5$

4a) Fmoc-Tyr-D-Ser[Rha(Ac$_3$)]-Leu-Arg-Pro-NH-C$_2$H$_5$ 1.76 g of DCC are added at 0° C. to a solution of 3.23 g of Fmoc-Tyr-OH, 7.54 g of H-D-Ser[Rha(Ac:)]-Leu-Arg-Pro-NH-C$_2$H$_5$ tosylate and 1.1 g of HOBt in 40 ml of dimethylformamide. The mixture is left to stir at 0° C. for 1 hour and at room temperature overnight. The precipitate is filtered off with suction, and the filtrate is concentrated. The residue is partitioned between n-pentanol and saturated NaHCO$_3$ solution. The pentanol phase is extracted by shaking with saturated NaHCO$_3$ solution and water, neutralized with 1 N methanolic p-toluenesulfonic acid and concentrated. The residue is triturated with methyl tert.-butyl ether and filtered off with suction.

Yield: 10.5 g.
$[\alpha]^{21}_D = -40.6°$ (c=1, in methanol).

4b) H-Tyr-D-Ser[Rha(Ac:)]-Leu-Arg-Pro-NH-C$_2$H$_5$ tosylate 7.5 ml of diethylamine are added at room temperature to a solution of 9.96 g of Fmoc-Tyr-D-Ser[Rha(Ac:)]-Leu-Arg-Pro-NH-C$_2$H$_5$ in 30 ml of dimethylformamide. The mixture is stirred at room temperature for 15 minutes and concentrated. The residue is triturated with diethyl ether and filtered off with suction.

Yield: 8 6 g.
$[\alpha]^{23}_D = -51.6°$ (c=1, in methanol).

4c)
Ac-D-Nal-D-Phe-D-Phe-Ser-Tyr-D-Ser(Rha)-Leu-Arg-Pro-NH-C$_2$H$_5$ acetate 110 mg of DCC are added at 0° C. to a solution of 320 mg of Ac-D-Nal-D-Phe-D-Phe-Ser-OH, 404 mg of H-Tyr-D-Ser(Rha)-Leu-Arg-Pro-NH-C$_2$H$_5$ tosylate and 81.5 mg of HOObt in 7 ml of dimethylformamide. The mixture is left to stir at 0° C. for 1 hour and subsequently at room. temperature overnight. The precipitate is filtered off with suction, and the filtrate is concentrated. The residue is worked up in analogy to Example 2 (yield 420 mg) and purified in analogy to Example 3.

Yield: 153 mg.
$[\alpha]^{23}_D = -100.8°$ (c=1, in water).
Content of peptide base: 76%.

We claim:
1. A peptide of the formula I

Ac-D-Nal(2)-D-Phe-D-Phe-Ser-X-D-Ser(Rha)-Leu-Arg-Pro-Y  (I), in which
represents acetyl,
D-Nal(2) represents 3-(2-naphthyl)-D-alanine,
D-Phe represents D-phenylalanine,
Ser represents L-serine,
X represents L-tyrosine (Tyr) or L-histidine (His),
D-Ser(Rha) represents O-(α-L-rhamnopyranosyl)-D-serine,
Leu represents L-leucine,
Arg represents L-arginine,
Pro represents L-proline and Y represents glycinamide (Gly-NH$_2$), D-alaninamide (D-Ala-NH$_2$), azaglycinamide (Azgly-NH$_2$) or NH-C$_2$H$_5$,
as well as the physiologically acceptable salts thereof.

2. A peptide of the formula I as claimed in claim 1, in which X denotes Tyr or His and
   Y denotes Azgly-NHz or D-Ala-NH$_2$, as well as the physiologically acceptable salts thereof.

3. A pharmaceutical composition containing an effective amount of a peptide of the formula I as claimed in claim 1, or the physiologically acceptable salt thereof, and a physiologically acceptable vehicle.

4. A method for the treatment of gonadoliberin-, gonadotropin- and steroid-dependent diseases in a host in need of such treatment, which comprises administering an effective amount of a peptide of formula I as claimed in claim 1, or the physiologically acceptable salt thereof, and a carrier.

* * * * *